United States Patent [19]

Mastrototaro et al.

[11] Patent Number: 5,779,665
[45] Date of Patent: Jul. 14, 1998

[54] TRANSDERMAL INTRODUCER ASSEMBLY

[75] Inventors: John J. Mastrototaro, Los Angeles; Richard Lemos, Littlerock; Nannette M. Van Antwerp, Valencia; Edgardo C. Halili, Reseda, all of Calif.

[73] Assignee: Minimed Inc., Sylmar, Calif.

[21] Appl. No.: 848,476

[22] Filed: May 8, 1997

[51] Int. Cl.⁶ .................................................. A61M 31/00
[52] U.S. Cl. ........................... 604/51; 604/164; 604/264; 604/280; 604/272; 128/635
[58] Field of Search .................. 604/51, 53, 118, 604/158, 164, 48, 111, 160, 166, 168, 264, 272, 280, 900; 606/167, 181, 182; 128/635

[56] References Cited

U.S. PATENT DOCUMENTS

| | | |
|---|---|---|
| 4,562,751 | 1/1986 | Nason et al. |
| 4,678,408 | 7/1987 | Nason et al. |
| 4,685,903 | 8/1987 | Cable et al. |
| 4,710,176 | 12/1987 | Quick |
| 4,755,173 | 7/1988 | Konopka et al. |
| 5,176,662 | 1/1993 | Bartholomew et al. |
| 5,254,106 | 10/1993 | Feaster |
| 5,257,980 | 11/1993 | Van Antwerp et al. |
| 5,360,416 | 11/1994 | Ausherman et al. |
| 5,390,671 | 2/1995 | Lord et al. |
| 5,391,250 | 2/1995 | Cheney, II et al. |
| 5,425,717 | 6/1995 | Mohiuddin |
| 5,482,473 | 1/1996 | Lord et al. |
| 5,568,806 | 10/1996 | Cheney, II et al. |
| 5,584,813 | 12/1996 | Livingston et al. |
| 5,586,553 | 12/1996 | Halili et al. |

*Primary Examiner*—Michael Buiz
*Assistant Examiner*—N. Kent Gring
*Attorney, Agent, or Firm*—Kelly Bauersfeld Lowry & Kelley, LLP.

[57] ABSTRACT

A transdermal introducer assembly is provided for quick and easy transcutaneous placement of a medical tube on a patient with reduced patient discomfort. The introducer assembly comprises a medical tube segment defining a hollow lumen extending between a distal end for placement into the subcutaneous tissue and a proximal end disposed outside the patient. The tube segment is assembled in side-by-side relation with a hollow introducer needle, and includes an elongated introducer thread at the distal end thereof folded back for slide-fit reception into the open distal end of the introducer needle. In use, the introducer needle is deployed to pierce the patient's skin at a selected placement site and to carry the tube segment to the desired transcutaneous position, after which the introducer needle can be withdrawn and slidably separated from the introducer thread to leave the tube segment and thread in place on the patient. A window is formed in the tube segment near the distal end thereof and, in a preferred form, exposes a transcutaneous sensor carried within the tube segment to patient body fluids.

21 Claims, 3 Drawing Sheets

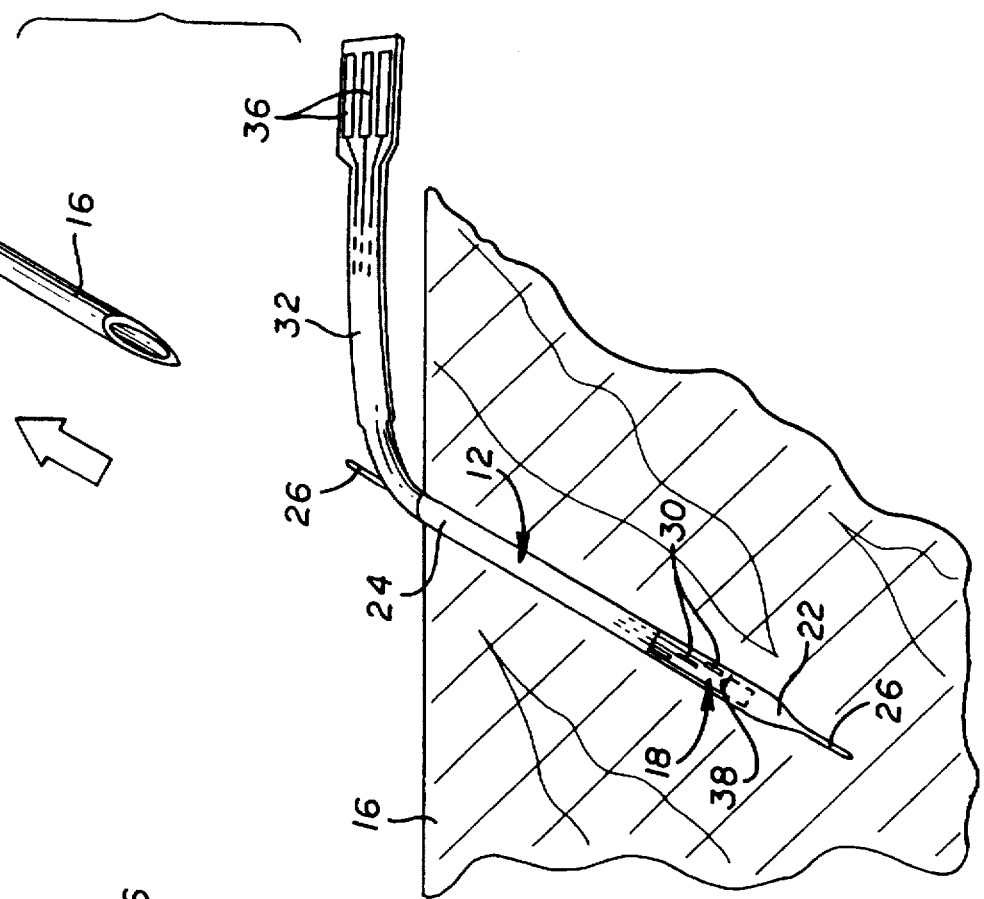
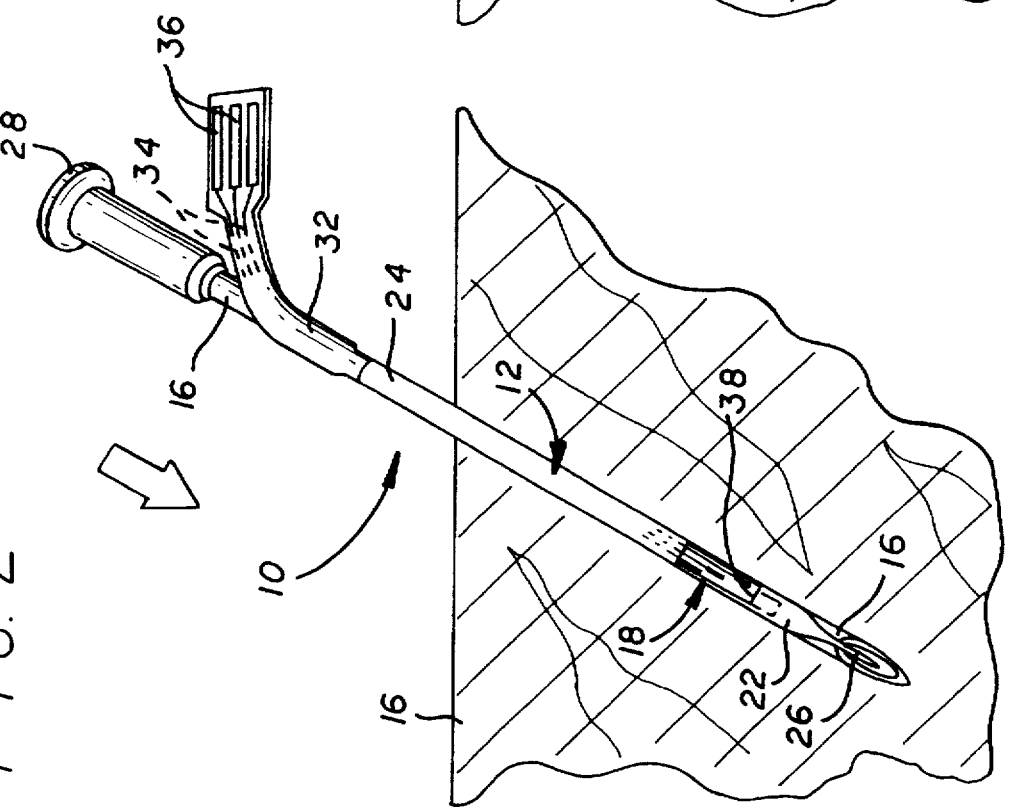

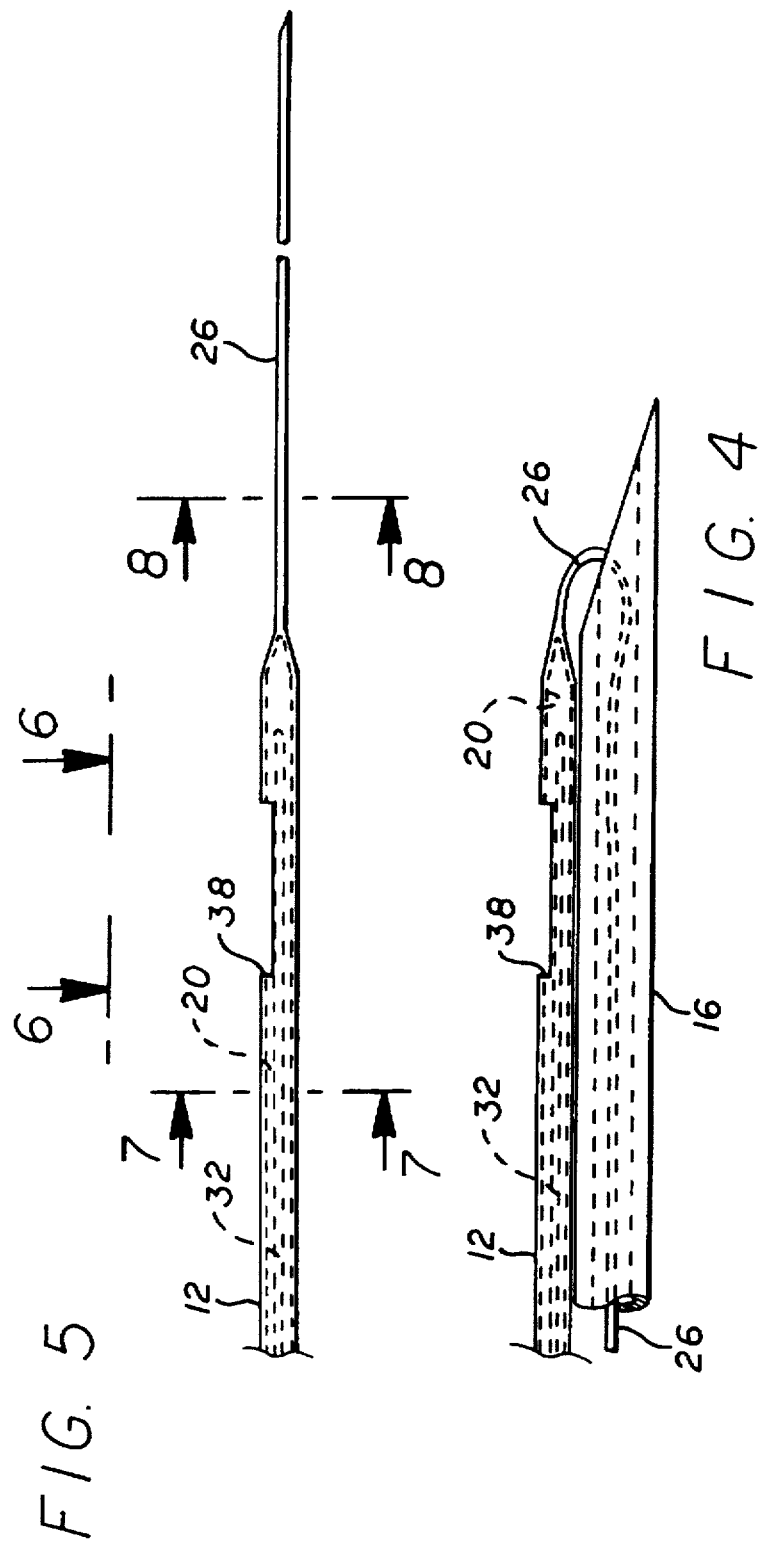
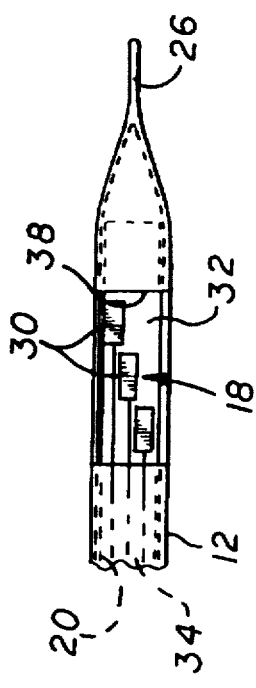

5,779,665

TRANSDERMAL INTRODUCER ASSEMBLY

BACKGROUND OF THE INVENTION

This invention relates generally to apparatus and methods for transdermal placement of medical devices on the skin of a patient. More particularly, this invention relates to an improved and relatively simple introducer assembly for quick and easy transcutaneous placement of a medical device such as a medical tube in a manner which substantially minimizes patient discomfort and trauma.

Transdermal insertion devices are generally known in the art for placing a medical device such as a medical tube or sensor at a selected subcutaneous position within the skin of a patient. These transdermal insertion devices typically comprise an introducer needle assembled with the medical device and adapted to pierce the patient's skin to carry the medical device to the desired subcutaneous location. In one common form, transdermal insertion devices have been used to place an infusion tube through the patient's skin, for subsequent infusion of medical fluids to the patient. See, for example, U.S. Pat. Nos. 4,755,173; 5,176,662; and 5,257,980. More recently, transdermal insertion devices have been used for subcutaneous placement of a miniature biological sensor of the type used, for example, to monitor blood glucose levels in a diabetic patient. See, for example, U.S. Pat. Nos. 5,391,250; 5,568,806; (insert patent no. for Minimed docket 34458); and U.S. Pat. No. 5,584,183.

Various mechanical structures and methods have been proposed in an effort to provide a transdermal insertion device having a simplified construction for facilitated and low cost manufacture in large quantities, while at the same time providing an insertion device which can be manipulated easily for rapid subcutaneous placement of the medical device with little or no patient discomfort and associated trauma. In this regard, it is generally desirable for the insertion device to utilize an introducer needle of small size for minimal patient discomfort, and to withdraw the introducer needle from the patient immediately upon subcutaneous placement of the medical device. Such insertion device constructions are typified by the various patents listed above.

There exists, however, an ongoing need for further improvements in and to transdermal introducer devices, particularly with respect to further structural simplifications to provide a lower cost device which remains compatible with the objective of minimum patient discomfort. The present invention relates to an improved introducer device which meets these objectives and provides further related advantages.

SUMMARY OF THE INVENTION

In accordance with the invention, an improved transdermal introducer assembly is provided for transcutaneous placement of a medical device such as a medical tube on a patient. The introducer assembly comprises a medical tube segment joined to an introducer thread which is threadably coupled with an introducer needle used to pierce the patient's skin and carry the tube segment to the desired subcutaneous position. Following placement of the tube segment, the introducer needle is adapted for quick and easy sliding removal from the introducer thread and tube segment to leave these components in place on the patient.

In the preferred form of the invention, the medical tube segment defines a relatively small cross sectional size with a hollow lumen extending between a distal end for subcutaneous placement on the patient, and a proximal end adapted to be positioned outside the patient. The distal end of the tube segment is joined preferably as an integral structure with the elongated introducer thread having a further narrowed cross sectional size. The size and length of the introducer thread is selected to fold back along the tube segment and to threadably engage the introducer needle. In the preferred form, the introducer needle is hollow to form an open distal end for slide-fit threaded reception of the introducer thread.

The introducer needle and the medical tube segment are assembled in side-by-side parallel relation, with the introducer thread coupled with the introducer needle. In this configuration, the introducer needle is manipulated to pierce the patient's skin at a selected placement site, whereby the needle carries the introducer thread together with the tube segment to the desired transcutaneous position. Following such placement of the tube segment, the introducer needle is quickly and easily withdrawn from the introducer thread in a sliding manner, leaving the introducer thread and associated tube segment in place on the patient.

In one preferred use, the tube segment has a biological sensor carried therein for transcutaneous placement therewith, such as a sensor of the type described in U.S. Pat. No. 5,391,250 which is incorporated by reference herein. The sensor includes one or more sensor electrodes formed generally at a distal end thereof for exposure to patient body fluids via an open window formed in the tube segment near the distal end thereof. These sensor electrodes are adapted for connection to suitable monitoring apparatus located outside the patient by means of appropriate conductive connectors formed at a proximal end of the sensor disposed outside the patient at the proximal end of the tube segment. Alternately, the lumen of the tube segment can be used for other purposes, such as to provide a path for infusing medical fluids to the patient.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is an enlarged fragmented vertical sectional view illustrating use of the introducer assembly of FIG. 1 to pierce the skin of a patient;

FIG. 3 is an enlarged fragmented vertical sectional view similar to FIG. 2, and depicting removal of an introducer needle following transcutaneous placement of the medical tube segment;

FIG. 4 is an enlarged fragmented side elevation view of a portion of the introducer assembly, showing assembly of the medical tube segment with the introducer needle;

FIG. 5 is a fragmented side elevation view of the medical tube segment prior to assembly with the introducer needle;

FIG. 6 is a fragmented top plan view of a portion of the medical tube segment, taken generally on the line 6—6 of FIG. 5;

3

Figure 8:

FIG. 8 is an enlarged transverse sectional view of the medical tube segment, taken generally on the line 8—8 of FIG. 6.

DETAILED DESCRIPTION OF THE PREFERRED EMBODIMENT

Figure 1:
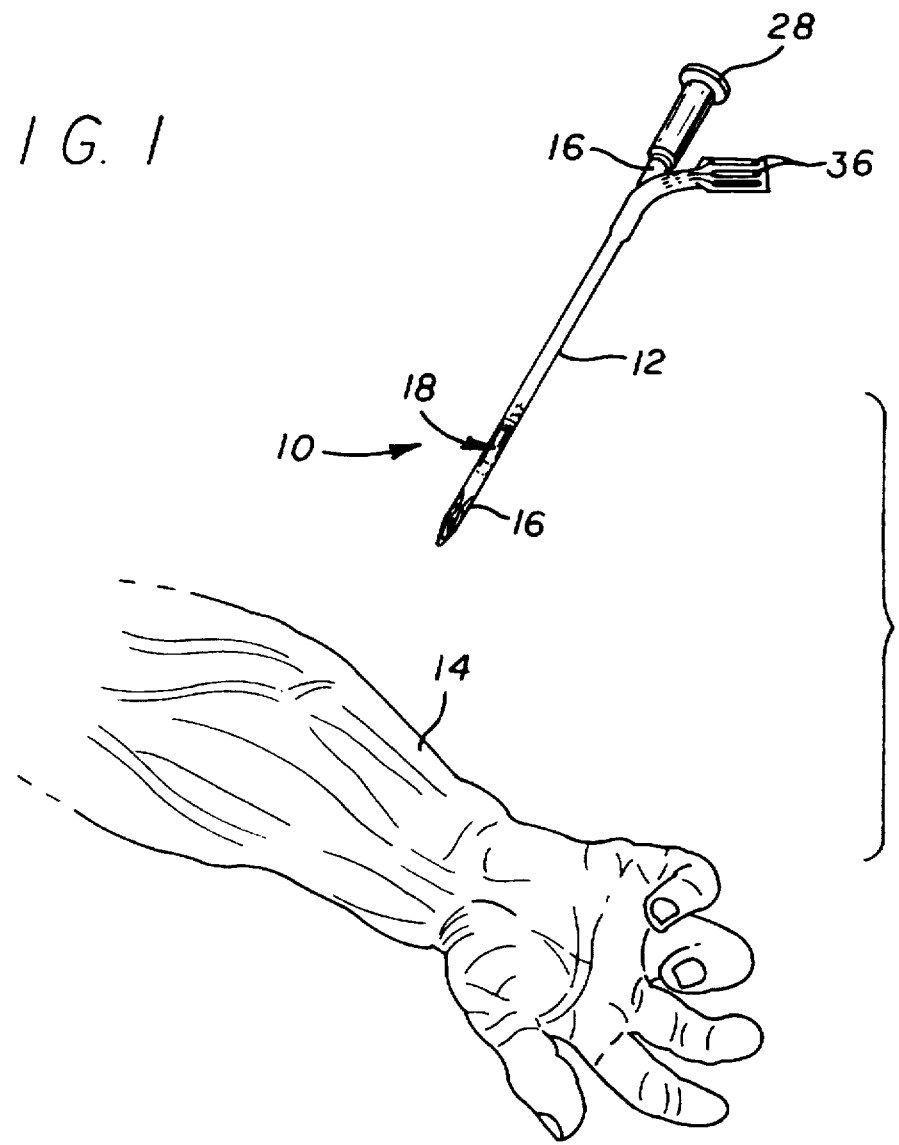
FIG. 1 is an exploded perspective view showing the transdermal introducer assembly of the present invention for use in placing a medical tube segment on a patient.
Figure 7:
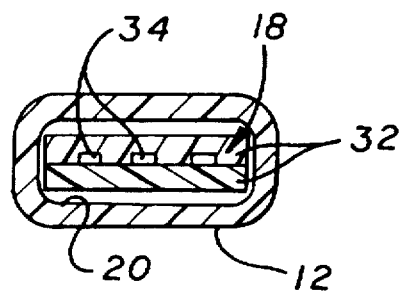
FIG. 7 is an enlarged transverse sectional view of the medical tube segment, taken generally on the line 7—7 of FIG. 6.

As shown in the exemplary drawings, an improved and relatively simplified transdermal introducer assembly referred to generally in FIG. 1 by the reference numeral 10 is provided for transcutaneous placement of a medical device such as a medical tube segment 12 on the skin 14 of a patient. The introducer assembly generally comprises a compact introducer needle 16 which is threadably assembled with the tube segment 12 for quick and easy transcutaneous placement of the tube segment, followed by quick and easy unthreading separation of the introducer needle to leave the medical tube segment 12 in place on the patient.

The transdermal introducer assembly 10 of the present invention is suited for facilitated and economical manufacture in large production quantities, with an introducer needle 16 and related medical tube segment 12 of extremely small size. As a result, the introducer assembly is designed for rapid and easy placement of the tube segment 12 on the patient with a minimum of patient discomfort and related patient trauma. When installed on the patient, the tube segment 12 can be used for a variety of medical purposes, such as supporting and retaining a biological sensor 18 (FIG. 6) as shown in the illustrative drawings and as will be described in more detail herein. Alternately, persons skilled in the art will recognize that the tube segment may be used for other medical purposes, including but not limited to providing a transcutaneous path for infusing medical fluids to the patient.

As shown best in FIGS. 4–8, the medical tube segment 12 comprises a length of medical grade tubing defining a hollow lumen 20. The tube segment 12 can be formed from a variety of tubing materials such as polyethylene or a selected polyurethane to have a lightweight and highly flexible construction in a small cross sectional size. In one example, the tube segment 12 is formed from extruded polyethylene to have a generally rectangular configuration (FIG. 7), with cross sectional dimensions on the order of about 0.026 inch by about 0.012 inch. Alternately, other small cross section geometries such as a circular shape or the like may be used. The length of the tube segment 12 is sufficient to extend between a distal end 22 for placement at the desired subcutaneous location to a proximal end 24 disposed outside the body of the patient, as viewed in FIGS. 2 and 3.

The distal end 22 of the tube segment 12 is joined to an elongated introducer thread 26 (FIGS. 4–6). In a preferred construction, this introducer thread 26 has a substantially narrowed or reduced cross sectional size compared to the outer diameter size of the tube segment 12, and may be formed as an integral component therewith by extruding the distal end of the tube segment to form the thread 26 as a generally coaxial extension of the tube segment. Alternately, the introducer thread 26 may be provided as a separate component mounted to the distal end 22 of the tube segment 12 as by use of a suitable bonding agent or the like. In either case, the thread 26 is also formed with substantial flexibility or resilience for threaded coupling with the introducer needle 16.

The introducer needle 16 comprises a hollow bore, small gauge medical needle having an open distal end which is appropriately beveled and sharpened to pierce the patient's

4 skin 14. A proximal end of the introducer needle 16 carries a suitable hub 28 (FIGS. 1–3) for manual handling and manipulation to transcutaneously place the tube segment 12, as will be described. The needle 16 is threadably assembled with the introducer thread 26, as viewed in FIG. 4, by slide-lifting the narrow thread 26 into the open distal end of the needle. While the gauge size of the introducer needle may vary, a needle 16 of 25 gauge size may be used for slide-in reception of the introducer thread 26 having a cross sectional diameter of about 0.009 inch.

With the introducer needle 16 and the medical tube segment 12 interconnected by the introducer thread 26, as described above, the introducer needle 16 and the tube segment 12 are oriented in close fitting side-by-side parallel relation (FIGS. 1–4) with the thread 26 folded back relative to the tube segment to fit into the bore of the needle 16. The illustrative rectangular cross section of the tube segment provides a geometry that is capable of lying closely against the outer diameter surface of the needle. In this orientation, the introducer needle 16 is employed to pierce the patient's skin 14 (FIG. 2) and concurrently to carry the tube segment 12 to the desired transcutaneous location on the patient. During such placement, the introducer thread 26 couples the tube segment 12 alongside the needle 16, with the distal end of the tube segment disposed slightly behind the point of the sharpened tip of the needle 16 to trail the needle tip as it pierces the skin. When the tube segment is properly placed, the introducer needle 16 is quickly and easily removed from the patient by simple slide-out withdrawal. Such withdrawal or separation of the needle 16 is accompanied by a sliding separation of the needle from the introducer thread 26, thereby leaving the thread 26 and tube segment 12 in place on the patient (FIG. 3). As shown, the introducer thread 26 has a sufficient length to that a distal end thereof extends at least a short distance out of the patient tissue, for facilitated subsequent slide-out removal of the tube segment 12 and thread 26 as a unit, when desired. The introducer needle 16 may be modified to remove the knife edge at the heel or base of the beveled tip to prevent the bevel from slicing the introducer thread 26 during insertion.

The illustrative drawings show the tube segment 12 for use in supporting and positioning the sensor 18 in a desired transcutaneous position on the patient. More particularly, in this preferred use of the invention, a flexible thin film sensor can be installed by slide-fit mounting into the lumen 20 of the tube segment, prior to transcutaneous placement thereof. The thin film sensor 18 may be constructed according to U.S. Pat. No. 5,391,250, which is incorporated by reference herein, to include one or more sensor electrodes 30 (FIGS. 6–8) mounted at or near the distal end of a flexible sensor substrate 32 and coupled by appropriate conductors 34 embedded within the substrate 32 to connector pads 36 disposed at a proximal end of the substrate. These connector pads 36 may be coupled in turn to appropriate monitoring equipment (not shown) by a connector block (also not shown) of the type described in U.S. Pat. No. 5,482,473 which is also incorporated by reference herein.

The distal end of the sensor 18, and the electrodes 30 carried thereon, are exposed to patient body fluids at the subcutaneous location through a small laterally or radially open window 38 formed in the tube segment 12 near the distal end thereof. In use, the electrodes 30 provide electrical signals representative of a patient parameter, such as a reading of blood glucose level which can be utilized to determine appropriate dosage timing and rates for a medication such as insulin. Alternately, it will be understood and recognized that the medical tube segment 12 can be used for other medical purposes, such as providing an open transcutaneous pathway through which medical fluids can be infused to the patient. Moreover, it will be understood that the tube segment 12 may be formed with alternative fluid passage means by omitting the window 38 and constructing the tube segment 12 from a porous material which permits passage of patient body fluids into contact with the electrodes 30.

The transdermal introducer assembly of the present invention thus provides an extremely simple structure which can be extremely small in size for use in quick and easy transcutaneous placement of a medical device on a patient. The invention is particularly suited for transcutaneous placement of a medical tube which can be utilized in a wide variety of medical applications.

A variety of further modifications and improvements in and to the transdermal introducer assembly of the present invention will be apparent to those skilled in the art. Accordingly, no limitation on the invention is intended by way of the foregoing description and accompanying drawings, except as set forth in the appended claims.

What is claimed is:

1. A transdermal introducer assembly, comprising:
   a tube segment defining a hollow lumen extending between a distal end for placement into the subcutaneous tissue of a patient, and a proximal end for placement outside the patient, said tube segment including means for permitting passage of fluid into said lumen at least at the distal end thereof;
   an elongated flexible introducer thread connected to the distal end of said tube segment; and
   a hollow introducer needle having an open distal end sized for slide-fit reception of said introducer thread, said thread permitting said tube segment to be folded back to extend along said introducer needle in close fitting side-by-side relation, whereby manipulation of the introducer needle to pierce the patient's skin carries said tube segment to a transcutaneous position, said introducer needle being slidably withdrawable from said introducer thread to leave said introducer thread and said tube segment transcutaneously positioned on the patient.

2. The transdermal introducer assembly of claim 1 wherein said introducer needle has a hub mounted on a proximal end thereof.

3. The transdermal introducer assembly of claim 1 wherein said tube segment is formed from a resilient material.

4. The transdermal introducer assembly of claim 1 wherein said means for permitting fluid passage into said lumen comprises a window formed in said tube segment generally at the distal end thereof.

5. The transdermal introducer assembly of claim 4 wherein said window formed in said tube segment is radially open.

6. The transdermal introducer assembly of claim 1 wherein said introducer thread is formed integrally with said tube segment.

7. The transdermal introducer assembly of claim 6 wherein said introducer thread comprises an extrusion drawn from the distal end of said tube segment.

8. The transdermal introducer assembly of claim 1 wherein said introducer thread has a cross sectional size substantially less than the cross sectional size of said tube segment.

9. The transdermal introducer assembly of claim 1 wherein said introducer thread has a sufficient length so that a distal end thereof extends out of the patient's skin when said introducer needle is slidably separated therefrom.

10. The transdermal introducer assembly of claim 1 further including a biological sensor mounted within said tube segment lumen for exposure to patient body fluid.

11. A transdermal introducer assembly, comprising:
    a medical device for placement into the subcutaneous tissue of a patient;
    an introducer thread connected to said medical device; and
    an introducer needle including means for slide-fit threaded engagement with said introducer thread, said thread when engaged with said introducer needle permitting said medical device to be positioned in close fitting side-by-side relation with said needle in a position trailing a distal end of said needle, whereby manipulation of said introducer needle to pierce the patient's skin carries said medical device to a subcutaneous position, said introducer needle being slidably withdrawable from the patient's skin for slide-off separation from said introducer thread to leave said thread and said medical device on the patient.

12. The transdermal introducer assembly of claim 11 wherein said medical device comprises a tube segment defining a lumen for transcutaneous placement of the patient's skin.

13. The transdermal introducer assembly of claim 11 wherein said introducer thread and said medical device are integrally formed.

14. The transdermal introducer assembly of claim 11 wherein said introducer thread has a sufficient length so that a distal end thereof extends out of the patient's skin when said introducer needle is slidably separated therefrom.

15. The transdermal introducer assembly of claim 11 wherein said needle means for slide-fit threaded engagement with said introducer thread comprises a hollow bore formed in said introducer needle.

16. A transdermal introducer assembly, comprising:
    a tube segment defining a hollow lumen extending between a distal end for placement into the subcutaneous tissue of a patient, and a proximal end for placement outside the patient, said tube segment having a radially open window formed therein generally at the distal end thereof;
    an elongated flexible introducer thread connected to the distal end of said tube segment, said introducer thread being formed integrally with said tube segment as an extruded extension at the distal end thereof; and
    a hollow introducer needle having an open distal end sized for slide-fit reception of said introducer thread, said thread permitting said tube segment to be folded back to extend along said introducer needle in close fitting side-by-side relation, whereby manipulation of the introducer needle to pierce the patient's skin carries said tube segment to a transcutaneous position, said introducer needle being slidably withdrawable from said introducer thread to leave said introducer thread and said tube segment transcutaneously positioned on the patient.

17. A method of placing a medical device into the subcutaneous tissue of a patient, said method comprising the steps of:
    providing the medical device with an elongated introducer thread connected thereto;
    theadably coupling the introducer thread with an introducer needle;

piercing the patient's skin with the introducer needle, with the introducer thread coupled thereto, to carry the introducer thread and the medical device to a subcutaneous position on the patient; and withdrawing the introducer needle from the patient's skin to slidably separate the introducer needle from the introducer thread and thereby leave the introducer thread and the medical device on the patient.

18. The method of claim 17 wherein said providing step comprises forming the medical device as a tube segment with a hollow lumen formed therein.

19. The method of claim 18 wherein said providing step further comprises forming the introducer thread by extruding the distal end of the tube segment, and forming an open window in the tube segment generally at the distal end thereof.

20. The method of claim 17 wherein said threadably coupling step comprises slide-fit reception of the introducer thread into a hollow bore formed in the introducer needle.

21. The method of claim 17 wherein said providing step further comprises forming the introducer thread with a sufficient length so that a distal end thereof extends out of the patient's skin when said introducer needle is slidably separated therefrom.

* * * * *